United States Patent [19]

Langford et al.

[11] Patent Number: Plant 7,336

[45] Date of Patent: Sep. 25, 1990

[54] PEACH TREE (SNOW DIAMOND)

[75] Inventors: Mitchell Langford; Rose M. Langford, both of Reedley; Vernon Langford, Woodlake, all of Calif.

[73] Assignee: Plum-Cot, Inc., Calif.

[21] Appl. No.: 355,647

[22] Filed: May 22, 1989

[51] Int. Cl.[5] ..... A01H 5/00

[52] U.S. Cl. ..... Plt./42

[58] Field of Search ..... Plt./42

*Primary Examiner*—Howard J. Locker

*Attorney, Agent, or Firm*—Townsend and Townsend

[57] ABSTRACT

The present invention relates to a peach tree and more particularly to a new and distinct variety broadly characterized by a large size, vigorous, hardy, productive and regular bearing tree. The fruit matures under the ecological conditions described approximately the last week in July, with first picking on July 27, 1988. The fruit is white in flesh color, large and uniform in size, freestone in types, firm in texture for good quality storage and shipping, mostly red in skin color, and sweet nonacid in flavor. The variety was discovered as a perchance seedling occurring near a Babcock (Unpatented) peach tree located adjacent to a commercial May Grand (U.S. Plant Pat. No. 2,794) nectarine orchard. Subsequent to origination of the present variety of peach tree, it was asexually reproduced by budding and grafting, and such reproduction of plant and fruit characteristics were true to the original plant in all respects.

No Drawings

BACKGROUND OF THE VARIETY

The present variety of peach tree, denominated varietally as "Snow Diamond", was discovered by us in 1981 in a cultivated area of an orchard owned at that time by Mitchell Langford and Rose Marie Langford and located at 17047 E. Dinuba Avenue, Reedley, Calif., in the County of Fresno located in the San Joaquin Valley. It resulted as a voluntary seedling that sprouted near a Babcock (unpatented) peach tree adjacent to a commercial nectarine planting of May Grand (U.S. Plant Pat. No. 2,794). Subsequent to the discovery of the present variety of peach tree, we asexually reproduced it by budding and grafting, and such reproduction of plant and fruit characteristics were true to the original plant in all respects.

The present variety most nearly resembles the Babcock (unpatented) peach variety in appearance by producing whiteflesh freestone fruit with excellent flavor and large size, but is distinguished therefrom and an improvement thereon by bearing fruit that harvests approximately two weeks later, has more red skin color, has a smaller stone, and most importantly has much firmer flesh. This high degree of firmness distinguishes the present variety as a commercial long distant shipping whiteflesh peach, which has not heretofore been sufficiently available in supermarkets in the United States.

The differences between the present variety and the May Grand (U.S. Plant Pat. No. 2,794) nectarine are very pronounced, as the present variety is a peach instead of a nectarine, has white flesh instead of yellow flesh, and ripens approximately five weeks later. It is virtually certain that the seed parent of the present variety was the Babcock peach, due to the proximity of the original seedling and its similarity in fruit characteristics. The pollen parent is unknown and its determination would be speculative.

DRAWING

The accompanying photograph shows the characteristics of the whole fruit in skin color and form, a characteristic fruit divided on its suture plane showing the flesh and pit cavity, a typical stone, and typical leaves.

POMOLOGICAL CHARACTERISTICS

Referring now more specifically to the pomological characteristics of this new and distinct variety of peach tree, the following has been observed under the ecological conditions prevailing near Reedley, Fresno County (San Joaquin Valley), Calif., and was developed at the state of eating ripe on July 29, 1988. All major color code designations are by reference to the Inter-Society Color Council, National Bureau of Standards. Common color names are also used occasionally.

TREE

Size: Large.
Vigor: Vigorous.
Growth: Spreading and dense.
Form: Round topped.
Hardiness: Hardy.
Production: Very productive.
Bearing: Regular bearer.
Trunk:
- *Size.*—Stocky.
- *Texture.*—Medium.
- *Color.*—Medium gray [265. med.Gy].
- *Lenticels:*—Numerous. Color: Light brown [57. l.Br]. Size: ⅛" to ⅜", [3.175–9.525 mm].

Branches:
- *Size.*—Medium.
- *Texture.*—Medium.
- *Color.*—1st Year Wood— Topside: Strong yellow green [117. s.YG] with some slight Grayish pink [8. gy.Pk] tinting. 1st Year Wood— Underside: Strong yellow green [117 s.YG]. Older Wood: Light grayish reddish brown [45 l.gy.rBr].
- *Lenticels.*—Numerous, small. Color: Strong yellowish brown [74. s.yBr].

Leaves:
*Size.*—Large. Average Length: 6.0" [152.4 mm.]. Average Width: 1½" [38.1 mm.].
*Thickness.*—Medium.
*Form.*—Elliptical.
*Apex.*—Acutely pointed.
*Base.*—Acute.
*Surface.*—Smooth.
*Color.*—Dorsal surface: Dark olive green [126. d.OlG]. Ventral surface: Moderate yellow green [120. m.YG].
*Margin.*—Finely serrate.
*Venation.*—Pinnately net veined.
*Petiole.*—Average Length: ⅜" [9.525 mm.]. Average Thickness: 5/32" [3.969 mm.].
*Glands.*—Numbers: 2 to 4 per leaf. Position: Most oppositely positioned on petiole and base of blade. Size: Small. Form: Globose. Color: Strong yellow green [117. s.YG].
*Stipules.*—Numerous. Length: ⅛" [3.175 mm.].

Flower Buds:
*Hardiness.*—Hardy.
*Size.*—Medium.
*Length.*—Medium.
*Form.*—Free.
*Surface.*—Pubescent.

Flowers:
*Blooming period.*—Medium, as compared with other varieties.
*Size.*—Large.
*Color.*—Light pink [4. l.Pk].

FRUIT

Maturity when described: Hard ripe, July 29, 1988.
Date of first picking: July 27, 1988.
Date of last picking: Aug. 3, 1988.
Size: Uniform, large.
*Average diameter axially.*—2⅞" [73.03 mm].
*Average traversely in suture plane.*—2⅞" [73.03 mm].
Form: Uniform, symmetrical, globose.
*Longitudinal section form.*—Round, but slightly truncate at base.
*Transverse section through diameter.*—Round, with a slight hump at the suture.
Suture: An inconspicuous line extending from the base to slightly beyond the apex with a slight depresson on both sides of the pistil point.
Ventral surface: Rounded along the suture.
Lips: Slightly unequal.
Cavity: Flaring, elongated in the suture plane, suture showing on both sides but being characteristically sharp on one side.
Base: Cuneate and slightly truncate.
Apex: Short, depressed within the suture.
Pistil point: Some oblique and some apical.
Stem: Medium.
*Average length.*—⅜" [9.525 mm.].
*Average width.*—1/36" [4.763 mm.].

Skin:
*Thickness.*—Medium.
*Texture.*—Tough.
*Tenacity.*—Tenacious to flesh.
*Tendency to crack.*—Not observed as of yet.
*Color.*—From dark red [16. d.R] to dark pink [6. d.Pk] over a pale yellow [89. p.Y] background.

Down: Scant, short, does not roll up when rubbed.

Flesh:
*Color.*—Greenish white [153. gWhite] with moderate red [15. m.R] streaking toward the stone.
*Surface of the pit cavity.*—Covered with moderate red [15. m.R] fibers.
*Amygdalin.*—Scarce.
*Juice.*—Moderate, rich.
*Texture.*—Firm, fine, crisp.
*Fibers.*—Abundant, fine, tender.
*Ripens.*—Evenly.
*Flavor.*—Nonacid and sweet.
*Aroma.*—Very slight.
*Eating quality.*—Best.

STONE

Type: Freestone.
Form: Oval.
Base: Straight.
Apex: Rounded, but having a short, very sharp tip.
Sides: Equal.
Surface: Furrowed along the ventral edge, pitted toward the base, ridged generally closer to the apex.
Ridges: Jagged toward the apex.
Color: Dark yellowish Brown [78. d.yBr].
Pit wall: ¼" [6.35 mm.] thick.
Tendency to split: Very slight.
Kernel:
*Form.*—Oval.
*Taste.*—Bitter.
*Viable.*—Yes.
*Average width.*—½" [12.7 mm.].
*Average length.*—⅝" [15.875 mm.].
Pellicle color: Moderate brown [58. m.Br].
Amygdalin: Moderate.

USE

Market: Fresh and long distance shipping.
Keeping quality: Good to excellent.
Shipping quality: Good to excellent.
Resistance to insects: No unusual susceptibilities noted.
Resistance to diseases: No unusual susceptibilities noted.

Although the new variety of peach tree possesses the described characteristics under the ecological conditions at Reedley, Calif., in the central part of the San Joaquin Valley, it is to be expected that variations in these characteristics may occur when farmed in areas with different climatic conditions, different soils types, and/or varying cultural practices.

We claim:

1. A new and distinct variety of peach tree, substantially as illustrated and described, which bears white-flesh freestone fruit that is large and uniform in size, mostly red in skin color, firm in texture, and which most nearly resembles the Babcock (unpatented) variety, but is distinguished from and an improvement of that variety by bearing fruit that has a higher degree of red skin color, has a smaller stone, matures approximately two weeks later, and is very much firmer and more suitable for long distance shipping by the commercial grower.

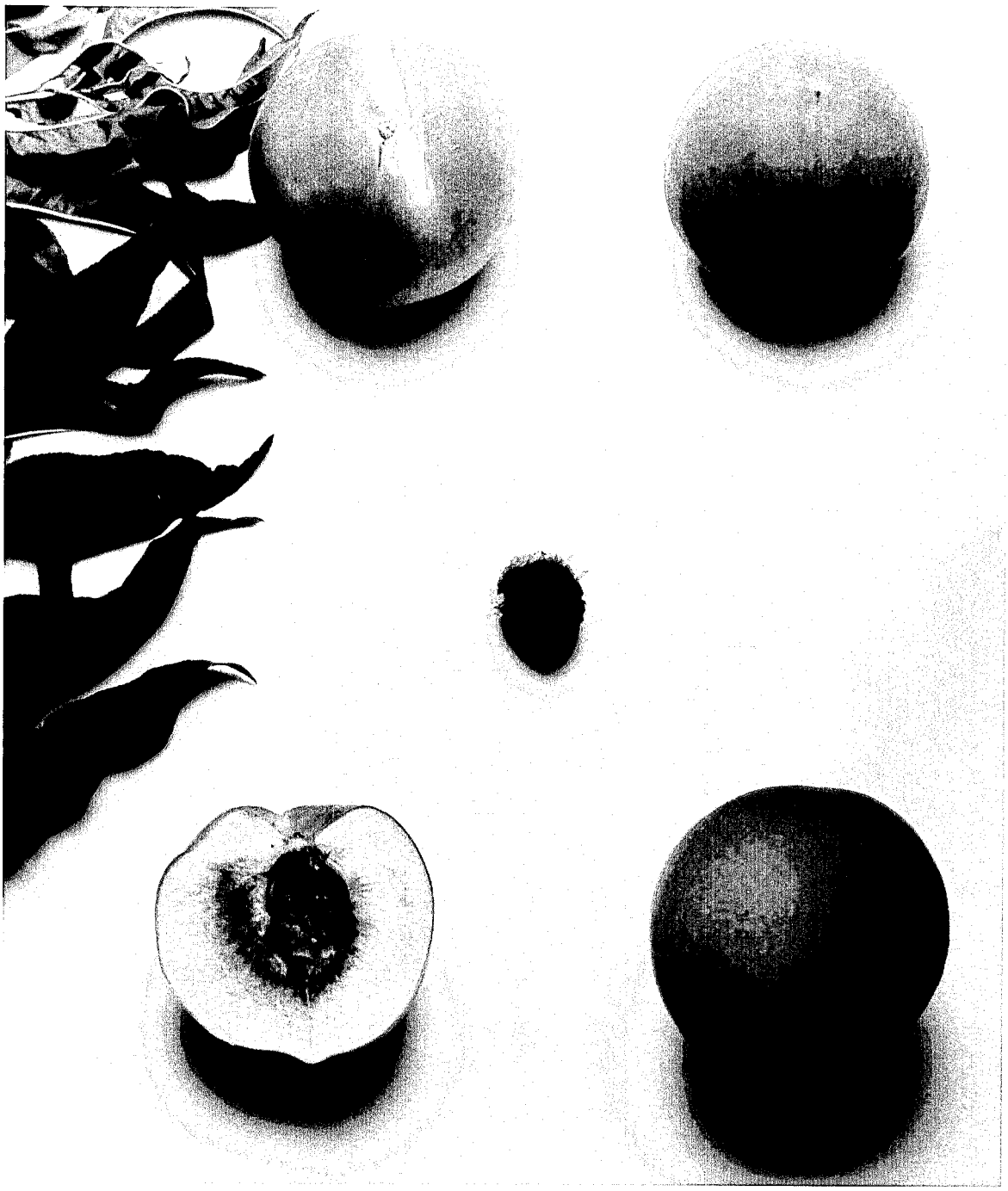

* * * * *